United States Patent [19] [11] 4,355,026
Umezawa et al. [45] Oct. 19, 1982

[54] 4-DEMETHOXY,11-DEOXY ANTHRACYCLINE DERIVATIVES

[75] Inventors: Hamao Umezawa; Tomio Takeuchi; Hiroshi Naganawa; Kuniaki Tatsuta, all of Tokyo, Japan

[73] Assignee: Zaidan Hojin Biseibutsu Kagaku Kenkyu Kai, Tokyo, Japan

[21] Appl. No.: 300,874

[22] Filed: Sep. 11, 1981

[30] Foreign Application Priority Data

Sep. 22, 1980 [JP] Japan ............................. 55-130645

[51] Int. Cl.³ .................... A61K 31/71; C07H 15/24; A61K 31/65
[52] U.S. Cl. .................................. 424/180; 260/365; 424/227; 536/6.4
[58] Field of Search ............. 424/180, 227; 536/17 A; 260/365

[56] References Cited

U.S. PATENT DOCUMENTS

| | | |
|---|---|---|
| 3,590,028 | 6/1971 | Arcamone et al. ............... 536/17 A |
| 3,616,242 | 10/1971 | Belloc et al. ..................... 536/17 A |
| 4,020,270 | 4/1977 | Arcamone et al. ............... 536/17 A |
| 4,025,623 | 5/1977 | Arcamone et al. ............... 536/17 A |
| 4,077,988 | 3/1978 | Arcamone et al. ................ 260/365 |
| 4,132,721 | 1/1979 | Bernardi ............................ 260/365 |
| 4,247,545 | 1/1981 | Cassinelli et al. ................ 536/17 A |

FOREIGN PATENT DOCUMENTS 2067552  7/1981  United Kingdom ............. 536/17 A

OTHER PUBLICATIONS

Arcamone et al., "Journ. of the Amer. Chem. Soc." vol. 102, No. 4, Feb. 13, 1980.

Primary Examiner—Johnnie R. Brown
Attorney, Agent, or Firm—David M. Morse

[57] ABSTRACT

New 4-demethoxy-11-deoxydaunomycin and 4-demethoxy-11-deoxyadriamycin anthracycline derivatives have been prepared and found to be useful antimicrobial and antitumor agents.

21 Claims, No Drawings

4-DEMETHOXY,11-DEOXY ANTHRACYCLINE DERIVATIVES

BACKGROUND OF THE INVENTION

1. Field of the Invention

This invention relates to new anthracycline derivatives, to methods for their use as antimicrobial and antitumor agents, to pharmaceutical compositions containing them and to synthetic methods and intermediates for the preparation of said new derivatives.

2. Description of the Prior Art

Daunomycin (see U.S. Pat. No. 3,616,242) and adriamycin (see U.S. Pat. No. 3,590,028) obtained from fermentation broths of microorganisms of the genus Actinomyces are known as anthracycline-type antibiotics. These compounds have a broad antitumor spectrum against experimental tumors and are widely used clinically as chemotherapeutic antitumor agents.

Despite the usefulness of daunomycin and adriamycin, there is still a need for new anthracycline derivatives which will have greater antitumor activity and/or reduced toxicities. To satisfy this need, attempts have been made to provide anthracycline derivatives by fermentation, biotransformation and both semisynthetic and total synthetic processes. Illustrative of these attempts are the methods disclosed by F. Arcamone in *Topics in Antibiotic Chemistry* 2:102-279 (1978) and in U.S. Pat. No. 3,988,315 (aclacinomycins A and B).

U.S. Pat. No. 4,247,545 discloses the preparation of 11-deoxy derivatives of daunomycin and adriamycin (as well as their respective aglycones) by fermentation of *Streptomyces peucetius* var. *caesius* (ATCC 31366).

SUMMARY OF THE INVENTION

This invention relates to novel anthracycline glycoside antibiotics having the formula

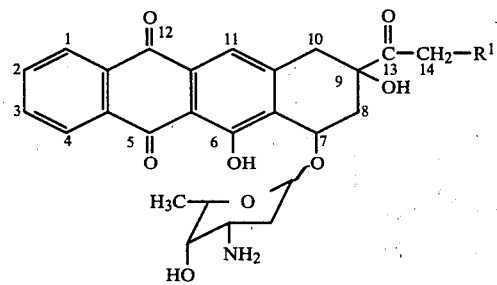

wherein $R^1$ is hydrogen, hydroxyl or (lower)alkanoyloxy, and nontoxic acid addition salts thereof, and to their respective aglycones having the formula

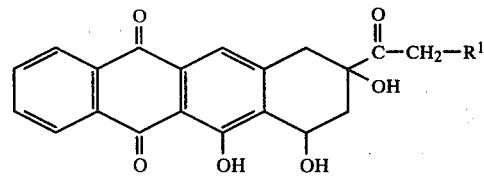

wherein $R^1$ is as defined above. The compounds included within the scope of formula I exhibit both antimicrobial and antitumor activity. The formula II aglycone compounds are important intermediates in preparation of the anthracycline end-products of formula I. Compounds of formula I in which $R^1$ is (lower)alkanoyloxy are also intermediates in preparation of the formula I products in which $R^1$ is hydroxy. In tests with experimental animal tumors, the preferred formula I compounds (i.e. those in which $R^1$ is H or OH) display especially strong antitumor activity.

As used herein and in the claims the term "non-toxic acid addition salt" is meant to include all those organic and inorganic acid salts of the compounds of formula I which are conventionally used as substantially nontoxic salts of medicinal agents containing amine functions. Illustrative examples would be those salts formed from such pharmaceutically acceptable acids as hydrochloric, hydrobromic, sulfuric, phosphoric, acetic, propionic, maleic, oleic, palmitic, citric, succinic, tartaric, fumaric, glutamic, pantothenic, laurylsulfonic, methanesulfonic and naphthalenesulfonic. The term "(lower)alkyl" as used herein includes both straight and branched chain saturated aliphatic hydrocarbon radicals having from 1-6, preferably 1-4, carbon atoms inclusive, e.g. methyl, ethyl, n-propyl, isopropyl, n-butyl, isobutyl, sec-butyl, tert-butyl, n-pentyl, isopentyl, n-hexyl, etc. Similarly, the term "(lower)alkanoyloxy group" denotes a residue of an alkanoic acid whose alkyl moiety is linear or branched and contains 1-5, preferably 1-3, carbon atoms. Examples of such groups include acetoxy, propionyloxy, n-butyryloxy, isobutyryloxy, n-valeryloxy and isovaleryloxy. The acetoxy group is an especially preferred alkanoyloxy group.

The compounds of the present invention may exist as the individual diastereomers or as mixtures of such isomers. It is specifically intended that the invention include the resolved diastereomers as well as mixtures of such diastereomers within its scope.

DETAILED DESCRIPTION

The compounds of the present invention may be prepared by total synthesis from 5-methoxy-2-tetralone, a known compound, by the synthetic route shown in the following reaction scheme.

REACTION SCHEME

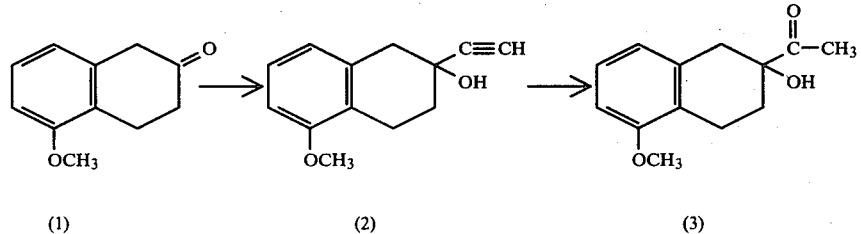

-continued
REACTION SCHEME
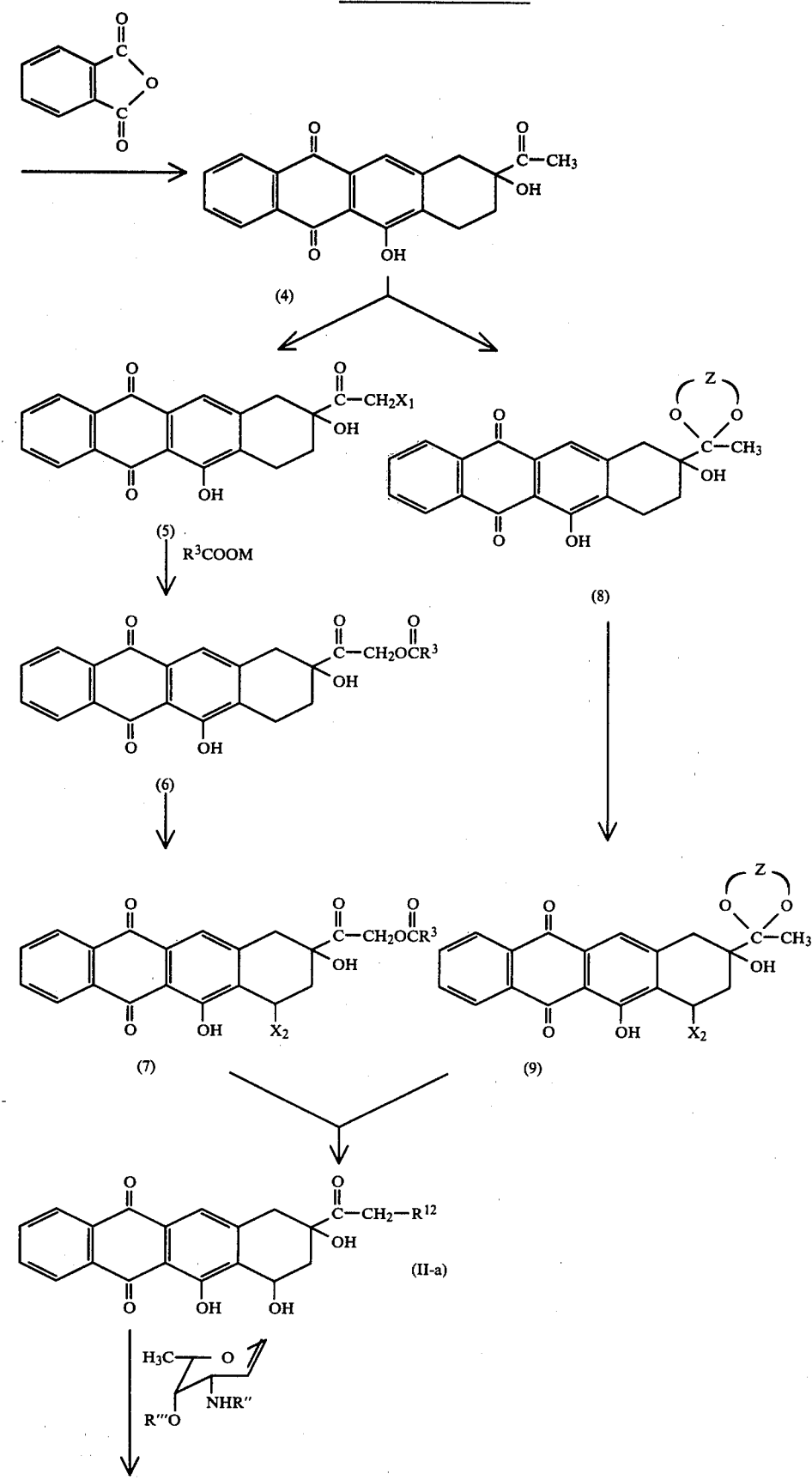

-continued
REACTION SCHEME

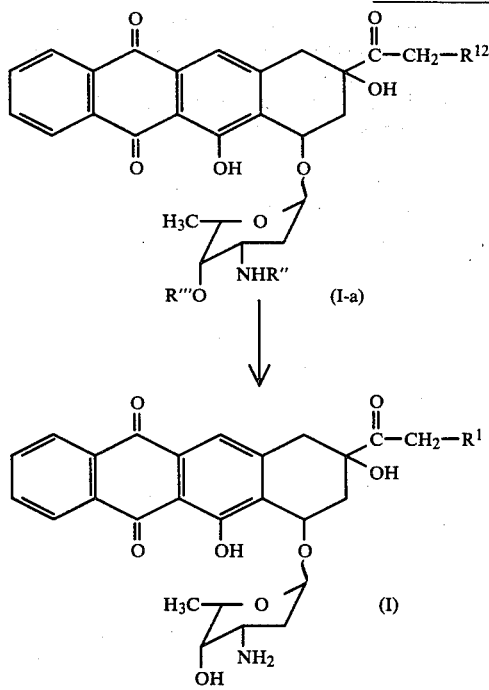

In the above reaction scheme, $R^1$ is as defined above, $R^{12}$ represents a hydrogen atom or a (lower)alkanoyloxy group, $R^3$ represents a (lower)alkyl group, $X_1$ and $X_2$ represent a halogen atom (Cl, Br, F, I), especially a bromine atom, Z represents a ketal residue, M represents an alkali metal atom, an alkaline earth metal atom or an ammonium group, and $R''$ and $R'''$ respectively represent a conventional amino-protecting group and a conventional hydroxyl-protecting group which can be easily eliminated by hydrolysis.

Each of the individual steps shown in the above reaction scheme may be practiced by known methods. The reactions in the individual steps are further elaborated on below.

(1)→(2)

In this step, 5-methoxy-2-tetralone of formula (1) is reacted with a Grignard reagent of the formula (CH≡C)MgX$_3$ wherein X$_3$ represents a halogen atom, preferably a bromine atom, to yield a tetraline derivative (2). This reaction can be carried out by utilizing a known Grignard reaction, for example as shown below in Step A of Example 1.

(2)→(3)

In this step, hydrolysis of the tetraline derivative (2) gives 2-acetyl-2-hydroxy-5-methoxy-1,2,3,4-tetrahydronaphthalene. The hydrolysis can be carried out, for example, by treating compound (2) with sulfuric acid in the presence of mercuric oxide, most advantageously at room temperature. The resulting compound (3) can be isolated from the reaction mixture by a conventional purification procedure, for example chromatography.

(3)→(4)

In this step compound (3) is reacted with phthalic anhydride to give 4-demethoxy-7,11-dideoxydaunomycinone (4). The Friedel-Crafts acylation may be conducted according to the general procedure disclosed in Experientia 34:1255-1257 (1978). For example, the reaction can be carried out in the presence of a Lewis acid such as aluminum chloride, titanium tetrachloride or zinc chloride at a temperature of from about 50° to 250° C., preferably 150°-200° C., for a period of from about 1 to 30 minutes, preferably about 5 to 10 minutes. The phthalic anhydride is used in an amount of at least one mole, preferably 1.5 to 2 moles, per mole of compound (3). The Lewis acid is used in an amount of at least 8 equivalents, preferably 12 to 20 equivalents, per mole of compound (3). Most preferably, the Friedel-Crafts acylation is carried out in the absence of a solvent at a relatively high temperature at which the starting materials substantially melt, i.e. at least above 150° C. and preferably 170° to 190° C. This effectively prevents the occurrence of the side reaction mentioned below.

If the Friedel-Crafts reaction is carried out in the presence of a conventional organic solvent or at a relatively low temperature (less than about 140° C.), a compound of the formula

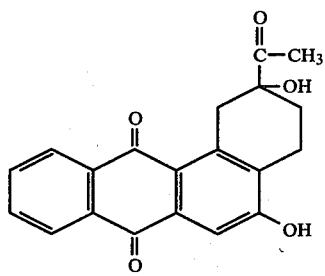

forms as a by-product in addition to the desired compound (4) and decreases the yield of (4). It has been found that if the reaction is carried out in the absence of solvent and at a relatively high temperature, the compound (4) can be obtained selectively in high yield without the formation of undesired by-product.

(4)→(5)→(6)

This reaction can be carried out in a manner known per se, for example by the method described in U.S. Pat. No. 3,803,124. Alternatively, the halogenation of compound (4) can be carried out by using an N-haloacid imide such as N-bromosuccinimide or N-chlorosuccinimide, preferably N-bromosuccinimide, resulting in selective halogenation of the 14-position of compound (4). Halogenation with the N-haloacid imide can be carried out at a temperature of from about 0° to 50° C. for a period of from about 2 to 10 hours. The amount of the N-haloacid imide used is not critical; advantageously, it is employed in an amount of at least 2 moles, preferably 8 to 16 moles, per mole of compound (4).

The acylation of compound (5) with a salt of an organic carboxylic acid having the formula $R^3COOM$ can be carried out at a temperature of from about 0° to 80° C. for a period of from about 5 to 20 hours. Preferably there is employed an inert solvent such as a ketone (e.g. acetone or methyl isobutyl ketone) or an ether (e.g. tetrahydrofuran or dioxane) either alone or as a mixture. The acylating agent is generally used in an amount of at least 1.5 moles, preferably 2 to 4 moles, per mole of compound (5). Examples of suitable acylating agents include sodium acetate, potassium acetate, ammonium acetate, sodium propionate, potassium propionate, ammonium propionate, sodium valerate and ammonium valerate.

(4)→(8)

The reaction in this step is ketalization of the carbonyl group at the 13-position of compound (4) which can be carried out in a manner known per se using a carbonyl protecting reagent (ketalizing reagent) known per se. For example, ketalization can be performed by the action of a ketalizing agent of the formula HO-Z-OH on compound (4) in a suitable inert solvent in the presence of an acid catalyst, for example an aromatic sulfonic acid such as p-toluenesulfonic acid or benzenesulfonic acid. The reaction temperature is not critical. Generally, it is preferred to use temperatures of from about room temperature to the reflux temperature of the reaction mixture, most preferably a temperature of from about 80° C. to reflux temperature. The ketalizing agent is used in an amount of at least 1.5 moles, preferably from about 5 to 15 moles, per mole of compound (4).

Specific examples of the ketal residue Z which may be employed are —CH₂CH₂—,

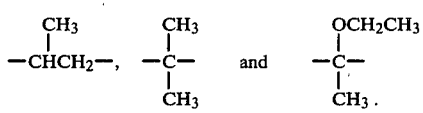

Specific examples of suitable ketalizing agents include ethylene glycol, propylene glycol, 1,1-dimethoxypropane and triethoxymethane.

(6)→(7) and (8)→(9)

These steps involve halogenation of the 7-position of compound (6) or compound (8). The halogenation can be carried out by using known halogenating agents such as bromine, chlorine, N-bromosuccinimide or N-chlorosuccinimide in a conventional manner. Bromination is especially preferred.

In a preferred embodiment, a solution containing bromine is added to compound (6) or (8) in an aqueous medium in the presence of a free radical generator such as 2,2-azobisisobutyronitrile (abbreviated AIBN) and the reaction is carried out at a temperature in the range of about 0° to 60° C., preferably at room temperature, for a period of from about 1 to 10 hours. Advantageously, at least 1.5 moles, preferably 2 to 3 moles, of bromine is used per mole of compound (6) or (8).

(7) or (9)→(II-a)

The reaction in this step is hydrolysis. Since compounds (7) and (9) are unstable, when the above halogenation step is carried out in the presence of water, the hydrolysis of compound (7) or (9) readily occurs to give the corresponding compound of formula II-a. The above hydrolysis may be conducted by a conventional method using an aqueous alkaline solution under mild conditions, for example at a relatively low temperature of from about room temperature to about 50° C. using a weak base such as sodium hydrogen carbonate.

When the hydrolysis of compound (7) is performed under relatively strong hydrolyzing conditions, for example by treating the compound with 10% $K_2CO_3$ at room temperature for one hour, a compound of formula II-a wherein $R^{12}$ is a hydroxyl group is formed.

Compound II-a is generally obtained as a mixture of four stereoisomers having the configurations (7S,9S), (7R,9R) (7R,9S) and (7S,9R). A racemic mixture (7S,9S; 7R,9R) and a racemic mixture (7R,9S; 7S,9R) can be easily separated from the stereoisomeric mixture of compounds II-a in a known manner, for example by a chromatographic technique.

It is expecially preferred that the desired end-product of formula I have the configuration (7S,9S). Accordingly, the separated racemic mixture (7R,9S; 7S,9R) of compound II-a can be epimerized to a racemic mixture (7S,9S; 7R,9R). As a result, the yield of the latter desired mixture can be increased. The epimerization may be carried out, for example, by contacting the above-mentioned racemic mixture of compound II-a with an inorganic acid such as hydrochloric acid or perchloric acid in a water-miscible organic solvent such as acetone, tetrahydrofuran or dioxane at a temperature of from about 10° C. to the boiling point of the solvent.

(II-a)→(I-a)

In this step the aglycone compound of formula II-a is reacted with a glycal of the formula

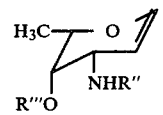

III derived from daunosamine to give a glycoside of formula I-a.

The amino-protecting group R'' in formula III is selected from conventional amino-protecting groups which are easily eliminated by hydrolysis. Specific examples include (lower)alkanoyl groups such as acetyl, propionyl and trifluoroacetyl, aromatic carbonyl groups such as benzoyl and p-nitrobenzoyl, aralkyloxycarbonyl groups such as benzyloxycarbonyl and alkyloxycarbonyl groups such as t-butoxycarbonyl. The hydroxy-protecting groups R''' are also selected from conventional hydroxy protecting groups which are easily eliminated by hydrolysis and may be similar to the groups mentioned above for the amino-protecting group R''.

The glycosidation reaction can be carried out in a conventional manner using an acid catalyst. Typically, it is carried out in an anhydrous inert organic solvent, e.g. benzene, toluene, tetrahydrofuran or dioxane, preferably in an aromatic hydrocarbon such as benzene or toluene, in the presence of an acid catalyst, for example an aromatic sulfonic acid such as p-toluenesulfonic acid or benzenesulfonic acid or an alkylsulfonic acid such as methanesulfonic acid or butanesulfonic acid. The reaction temperature is advantageously in the range of about 0° to 80° C., preferably about 20° to 40° C. It is preferred to use the compound of formula III in an amount of at least 1.5 moles, preferably 2 to 4 moles, per mole of compound II-a.

The glycal of formula III can be produced by treating a daunosamine derivative having the 3-amino group and the 4-hydroxyl group protected as described above with a sulfonylating agent such as p-toluenesulfonyl chloride or benzenesulfonyl chloride in the presence of a base such as pyridine, dimethylaniline, morpholine or triethylamine either in an organic solvent or in the absence of solvent (see Japanese Published Patent Application 27346/79.

The glycoside of formula I-a resulting from the above-described glycosidation reaction is usually obtained as a mixture of an isomer whose amino sugar residue has a 1'α linkage (to be referred to as a 1'α isomer) and an isomer whose amino sugar residue has a 1'β-linkage (to be referred to as a 1'β isomer) with the 1'α isomer generally predominating. Accordingly, when the racemic mixture (7S,9S; 7R,9R) of the compound II-a is used as a starting material, the glycoside of formula I-a is a mixture of four stereoisomers (7S,9S,1'α), (7S,9S,1'β), (7R,9R,1'α) and (7R,9R,1'β). These isomers may be separated by conventional procedures such as chromatography on silica gel or the like. Isolation of these stereoisomers is preferably performed after the de-protecting reaction to be described below.

(I-a→I)

This step is the elimination of the amino- and hydroxy-protecting groups of compound I-a. This deprotecting reaction is carried out by a conventional hydrolysis method. For example, it can be effected by alkaline hydrolysis at a relatively low temperature of from about 0° C. to room temperature in the presence of a base such as sodium carbonate or potassium carbonate. This hydrolysis results in the elimination of the protective groups R'' and R''' from compound I-a. When $R^{12}$ is a (lower)alkanoyloxy group, the lower alkanoyl group is also eliminated depending upon the conditions of hydrolysis to give a compound of formula I in which $R^1$ is OH.

By the above-described procedure, the anthracycline derivatives of formulae I and II may be obtained in good yield.

In a variation of the above procedure, a compound of formula I-a in which $R^{12}$ represents hydrogen can be converted to the corresponding compound of formula I-a in which $R^{12}$ is a (lower)alkanoyloxy group by subjecting it to the steps (4), (5) and (6) in the above-described sequence.

Products of formula I obtained in the above reaction procedures may be recovered in the form of the free base, an acid addition salt or a nontoxic acid addition salt. The free base products may be easily converted into nontoxic acid addition salts which are substantially equivalent in therapeutic activity to the corresponding free bases. The salts are formed, isolated, purified and formulated by the methods generally employed in salt formation for the anthracycline glycoside antibiotics. Thus, the free base may be reacted with a nontoxic organic or inorganic acid in a suitable solvent and the salt recovered by lyophilization or by precipitation with an antisolvent, i.e., a solvent in which the desired salt is only slightly insoluble. Products in the form of an acid addition salt may be converted to the corresponding free base by neutralization with a basic substance. Finally, toxic acid addition salts may be converted to nontoxic acid addition salts by neutralization and treatment with a nontoxic acid as described above.

The aglycone moiety shown in the compounds of the present invention is drawn in a planar structure, but is meant to include all configurations (7S,9S), (7R,9R), (7S,9R) and (7R,9S).

Biological Properties

The compounds of formula I, especially those in which $R^1$ is hydrogen or hydroxyl and nontoxic acid addition salts thereof, have shown excellent antitumor activity against L1210 leukemia cells in culture and experimental animal tumors. Especially preferred are those having the configuration (7S,9S) which is the same as daunomycin or adriamycin produced by fermentation. The glycoside moiety in the compounds of the present invention most preferably has a 1'α-linkage.

The antitumor activity of the compounds of formula I may be demonstrated by the following experiments.

A. Inhibitory Effect on Growth, DNA Synthesis and RNA Synthesis of L1210 Cultivated Leukemic Cells of Mice The compounds of formula I markedly inhibit the growth and nucleic acid synthesis of cultivated leukemic L1210 cells of mice. For example, L1210 cells were inoculated in a concentration of $5 \times 10^4$ cells/ml in an RPMI 1640 culture medium (Roswell Park Memorial Institute 1640) containing 20% calf serum and, simultaneously, representative compounds of the present invention were added in a concentration of 0.1 and 0.5 μg/ml. The cells were cultivated in a $CO_2$ generator at 37° C. The 50% growth inhibitory concentration with respect to a control group was then determined.

Separately, the above L1210 cultivated cells were suspended in a concentration of $5 \times 10^5$ cells/ml in an RPMI 1640 medium containing 10% calf serum and cultivated for 1 to 2 hours in a $CO_2$ incubator at 37° C. Then, representative test compounds were added in various concentrations, and 15 minutes later, $^{14}C$-uridine (0.05 μCi/ml) or $^{14}C$-thymidine (0.05 μCi/ml) were added. The cells were incubated at 37° C. for 60 minutes. A 10% aqueous trichloroacetic acid solution was added to the incubation medium to stop the reaction and simultaneously precipitate acid-insoluble matter. The acid-insoluble matter was washed three times with a 5 to 10% aqueous solution of trichloroacetic acid and then dissolved in formic acid. The radioactivity of the acid-insoluble matter was measured. From the ratio of incorporated radiation to that of a control group, the concentrations which inhibited radiation by 10%, 50% and 90% respectively were measured. The results are shown in Table 1 below.

the present invention against various microorganisms on a nutrient agar medium.

TABLE 1

Activity of the compounds of the invention to inhibit the growth, DNA synthesis and RNA synthesis of cultivated leukemic cells L1210 of mice

| COMPOUND | $IC_{50}(\mu g/ml)$ 1 day later | $IC_{50}(\mu g/ml)$ 2 days later | $IC_{50}(\mu g/ml)$ DNA | $IC_{50}(\mu g/ml)$ RNA | $IC_{10}(\mu g/mg)$ DNA | $IC_{10}(\mu g/mg)$ RNA | $IC_{90}(\mu g/mg)$ DNA | $IC_{90}(\mu g/mg)$ RNA |
|---|---|---|---|---|---|---|---|---|
| Daunomycin | 0.049 | 0.036 | 0.3 | 0.18 | 0.072 | 0.032 | 1.8 | 1.8 |
| Adriamycin | 0.05 | 0.03 | 1.65 | 0.68 | 0.19 | 0.12 | 4.5 | 6.5 |
| 4-Demethoxy-daunomycin | 0.01 | 0.005 | 0.08 | 0.14 | 0.007 | 0.017 | 1.2 | 1.4 |
| 11-deoxy-daunomycin | 0.05 | — | — | — | — | — | — | — |
| 4-Demethoxy-adriamycin | 0.02 | 0.006 | 1.6 | 1.2 | 0.12 | 0.15 | 10 | 6.0 |
| 11-Deoxy-adriamycin | 0.005 | — | — | — | — | — | — | — |
| 4-Demethoxy-11-deoxy-daunomycin | | | | | | | | |
| (7S,9S,1'α)isomer | 0.09 | 0.01 | 0.22 | 0.34 | 0.02 | 0.04 | 2.5 | 2.5 |
| (7S,9S,1'β)isomer | 1.4 | 0.51 | 3.1 | 5.4 | 0.46 | 0.9 | 15 | 14 |
| (7R,9R,1'α)isomer | >2.5 | >2.5 | 5.4 | 9.0 | 0.8 | 0.9 | 13 | >10 |
| (7R,9R,1'β)isomer | 2.0 | 1.25 | 4.5 | 5.0 | 0.6 | 0.8 | 15 | 13 |
| 4-Demethoxy-11-deoxy-adriamycin | | | | | | | | |
| (7S,9S,1'α)isomer | 0.07 | 0.03 | 0.64 | 0.8 | 0.07 | 0.08 | 5.6 | 4.6 |
| (7R,9R,1'α)isomer | 72.5 | 72.5 | >10 | >10 | 7.4 | 7.4 | >10 | >10 |

B. Antitumor Activity on CDFI Mouse Leukemia Induced by Mouse L1210 Leukemia cells L1210 leukemia cells of mice were intraperitoneally transplanted in an amount of $1 \times 10^5$ cells/mouse in CDFI mice. Starting 24 hours after the transplantation, each of the test compounds was intraperitoneally administered to the mice for 10 consecutive days. the survival rate (T/C, %) was calculated in comparison with a control group (to which physiological saline was administered). The results are shown in Table 2 below.

TABLE 2

Antitumor Activity (T/C, %)

Dosage (mg/kg/day,mouse) Survival rate (T/C, %)

| Compound | 5 | 2.5 | 1.25 | 0.6 | 0.3 | 0.15 |
|---|---|---|---|---|---|---|
| Daunomycin | dead through toxicity | 138 | 191 | 145 | 132 | 118 |
| Adriamycin | 189* | 351 | 272 | 239 | 147 | 130 |
| 4-Demethoxy-11-deoxydaunomycin (7S,9S,1'α) | — | 160 | 135 | 115 | 115 | 103 |
| 4-Demethoxy-11-deoxyadriamycin (7S,9S,1'α) | — | 177* | 308 | 184 | 162 | 135 |

*Toxicity

As can be seen from the above experimental results, the compounds of formula I provided by the present invention, expecially those in which $R^1$ is hydrogen or hydroxyl, exhibit excellent antitumor activity on L1210 leukemic cells and experimental animal tumors. The antitumor activity of the 4-demethoxy-11-deoxyadriamycin (7S,9S,1'α) stereoisomer is particularly noteworthy.

The compounds of formula I provided by the present invention are also characterized by their antimicrobial activity. Table 3 summarizes the minimum inhibitory concentrations (MIC) of representative compounds of

TABLE 3

MIC on various bacteria

| Bacteria | M.I.C. (μg/ml) Compound A | Compound B | Compound C | Compound D |
|---|---|---|---|---|
| Staphylococcus aureus FDA 209 | 25 | >100 | 100 | >100 |
| Staphylococcus aureus smith | 12.5 | >100 | 12.5 | >100 |
| Bacillus subtilis PCI 219 | 3.12 | 100 | 12.5 | >100 |
| Bacillus subtilis NRRB- 558 | 6.25 | 50 | 12.5 | >100 |
| Bacillus cereus ATCC 10702 | 12.5 | 50 | 25 | >100 |
| Bacillus megatherium APF | 6.25 | 50 | 12.5 | >100 |
| Sarcina lutea PCI 1001 | 6.25 | 50 | 100 | >100 |
| Microccus flavus FDA 16 | 6.25 | >100 | 50 | >100 |
| Microccus lysodeikticus IFQ 3333 | 12.5 | >100 | 50 | >100 |
| Corynebacterium bovis 1810 | 6.25 | 100 | 100 | >100 |
| Klebsiella pneumonia PCI 602 | 100 | >100 | >100 | >100 |
| Escherichia coli NIHJ | >100 | >100 | >100 | >100 |
| Salmonella typhi T - 63 | >100 | >100 | >100 | >100 |
| Shigella flexneri 46 JS 11811 | 100 | >100 | >100 | >100 |
| Pseudomonas aeruginosa A3 | >100 | >100 | >100 | >100 |
| Candida albicans 3147 | 100 | >100 | >100 | >100 |
| Mycobacterium smegmatis ATCC 607 | 12.5 | 100 | 12.5 | 100 |

Compound A: 4-Demethoxy-11-deoxydaunomycin, (7S,9S,1'α) isomer
Compound B: 4-Demethoxy-11-deoxydaunomycin, (7R,9R,1'α) isomer
Compound C: 4-Demethoxy-11-deoxyadriamycin, (7S,9S,1'α) isomer
Compound D: 4-Demethoxy-11-deoxyadriamycin, (7R,9R,1'α) isomer

Therapeutic Use

The compounds of formula I and their nontoxic acid addition salts possess activity as antimicrobial agents, useful in both human and veterinary medicine, and also marked inhibitory action against malignant mammalian tumors, including both solid and ascitic types.

According to one aspect of the invention, a method is provided for therapeutically treating a mammalian host affected by a microbial infection (particularly a gram-positive bacterial infection) or by a malignant tumor (i.e. a solid- or ascitic-type tumor such as L1210 leukemia) which comprises administering to said host an effective antimicrobial or tumor-inhibiting dose of a compound of formula I, or a nontoxic acid addition salt thereof.

According to another aspect of the invention, a pharmaceutical composition is provided which comprises a therapeutically effective antimicrobial or tumor-inhibiting amount of a compound of formula I, or a nontoxic acid addition salt thereof, in combination with a compatible pharmaceutical carrier or diluent. Preferably, such compositions are made up in a form appropriate for parenteral administration.

Preparations for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosage amounts used will vary according to the particular compound being used, the particular composition formulated, the mode of application and the particular situs, host and disease being treated. In general the compounds are administered intraperitoneally, subcutaneously, intravascularly (intravenously or intraarterially) or topically to non-human mammals and intravascularly or topically to humans. Many factors that modify the action of a drug will be taken into account by those skilled in the art, for example, age, body weight, sex, diet, time of administration, route of administration, rate of excretion, condition of the patient, drug combinations, reaction sensitivities and severity of the disease. Administration may be carried out continuously or periodically within the maximum tolerated dose. Optimal dosages and application rates for a given set of conditions can be ascertained by those skilled in the art using conventional dosage determination tests based on the above guidelines. Typically, the dosage will be about 0.2 to 5 mg/kg of body weight.

For use as an antimicrobial agent, the compounds are in general administered so that the concentration of active ingredient is greater than the minimum inhibitory concentration for the particular organism being treated. The number of administrations, dosage form, etc. may be easily determined by the skilled person using conventional dosage determination tests.

The following examples are provided for illustrative purposes only and are not intended to limit the scope of the present invention. In the examples, the ratio of solvent in a mixture is indicated in the ratio of volume to volume.

EXAMPLE 1

Production of 4-demethoxy-11-deoxydaunomycinone

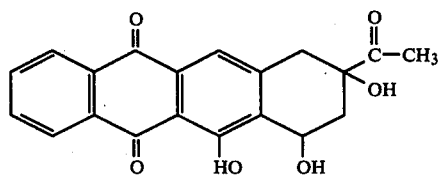

Step A

2-Ethinyl-2-hydroxy-5-methoxy-1,2,3,4-tetrahydronaphthalene

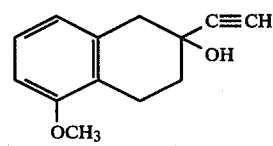

While acetylene was blown into 80 ml of anhydrous tetrahydrofuran, 36 ml of a 2 M ether solution of ethylmagnesium bromide was added dropwise.

To the resulting solution was added 2.88 g of 5-methoxy-2-tetralone. After the reaction, the reaction mixture was poured into 500 ml of a saturated aqueous solution of ammonium chloride, and the mixture was extracted with 200 ml of carbon tetrachloride three times. The extracts were washed with water, dried over sodium sulfate, and concentrated to dryness. The resulting brown oily product was chromatographed on a column of silica gel using benzene/ethyl acetate (25/1) as an eluent to give 1.6 g of the desired product as a brown oil.

| NMR$\delta$: 60 MHz, CDCl$_3$ | | |
|---|---|---|
| 1.9 ~ 2.3 | (m) | —CH$_2$— at 3-position |
| 2.4 0 | (s) | —C≡CH at 2-position |
| 2.4 2 | (s) | —OH at 2-position |
| 2.7 ~ 3.1 | (m) | —CH$_2$— at 4-position |
| 3.05 ~ 3.2 | (m) | —CH$_2$— at 1-position |
| 3.8 2 | (s) | —OCH$_3$ at 5-position |
| 6.6 ~ 7.35 | (m) | H at 6-,7- and 8-positions |

Step B

2-Acetyl-2-hydroxy-5-methoxy-1,2,3,4-tetrahydronaphthalene

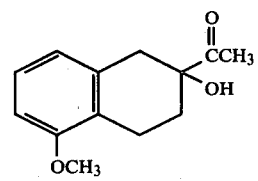

The compound of formula (2) was dissolved in 10 ml of carbon tetrachloride, and 10 ml of 1.5 N sulfuric acid and 200 mg of mercuric oxide were added. They were reacted at room temperature for 27 hours. Water (40 ml) was added, and the reaction mixture was extracted with 50 ml of carbon tetrachloride four times. The extracts were washed with water, dried over sodium sulfate, and concentrated to dryness. The resulting oily product was chromatographed on a column of silica gel using benzene/ethyl acetate (20/1) as an eluent to give 840 mg of the desired product as colorless needles.

Melting point: 63°-63.5° C.

| NMRδ: 60 MHz, CDCl3 | | |
|---|---|---|
| 1.8 ~ 2.1 | (m) | —CH2— at 3-position |
| 2.28 | (s) | COCH3 at 2-position |
| 2.5 ~ 3.5 | (m) | —CH2— at 1- and 4-positions |
| 3.45 | (s) | OH at 2-position |
| 3.83 | (s) | OCH3 at 5-position |
| 6.6 ~ 7.3 | (m) | H at 6-,7- and 8-positions |

Step C

4-Demethoxy-7,11-dideoxydaunomycinone

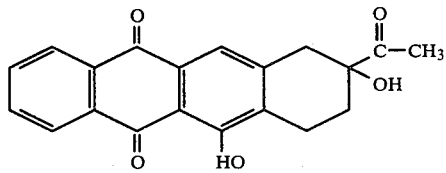

(4)

230 mg of the compound (3) obtained in step B, 230 mg of phthalic anhydride, 460 mg of sodium chloride and 2.3 g of aluminum chloride were well mixed, and melted by heating them to 180° C. In 1 to 2 minutes, the mixture became homogeneous, but it was reacted further for 5 minutes.

The reaction mixture was treated with a saturated aqueous solution of oxalic acid, and extracted with 30 ml of chloroform five times. The extracts were combined, washed with water, dried over sodium sulfate, and concentrated to dryness. The product was chromatographed on a column of silica gel using benzene/ethyl acetate (20/1) as an eluent to give 110 mg of the desired product as a yellow solid.

Melting point: 208°-214° C. (decomp.)

| NMRδ: 60 MHz, DMSO | | |
|---|---|---|
| 1.7 ~ 2.2 | (m) | —CH2— at 8-position |
| 2.30 | (s) | —COCH3 at 9-position |
| 2.6 ~ 3.1 | (m) | —CH2— 7- and 10-positions |
| 5.60 | (s) | —OH at 9- position |
| 7.38 | (s) | —H at 11 position |
| 7.8 ~ 8.4 | (m) | —H at 1-,2-,3- and 4 positions |
| 12.80 | (s) | —OH at 6-position |

Step D

Ketal derivative of the compound (4)

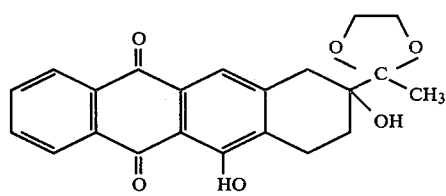

(8-a)

100 mg of the compound (4) was dissolved in 15 ml of benzene, and 0.3 ml of ethylene glycol and a catalytic amount of p-toluenesulfonic acid were added. The mixture was reacted for 3 hours under reflux. The reaction mixture was then poured into a 0.02 N aqueous solution of sodium hydrogen carbonate and extracted with 40 ml of ethyl acetate three times. The extracts were dried over sodium sulfate, and concentrated to dryness. The above reaction proceeded quantitatively.

Step E

4-Demethoxy-11-deoxydaunomycinone

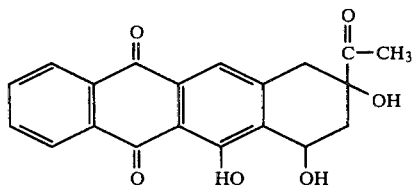

The ketal compound (8-a) obtained in step D was dissolved in chloroform, and 12.6 ml of a 0.8% (W/V) bromine in carbon tetrachloride solution, 21 ml of water and 120 mg of azobisisobutyronitrile were added. The reaction mixture was reacted at room temperature for 3.5 hours. After the reaction, 4 ml of the above bromine solution was further added, and the reaction was carried out for 2 hours. After the reaction, bromine, carbon tetrachloride and chloroform were distilled off from the reaction mixture. The residue was dissolved in 120 ml of acetone, and 21 ml of 8 N hydrochloric acid was added. The reaction was carried out at room temperature for 18 hours [deprotection of the ketal, and the epimerization of (7S,9R; 7R,9S) to (7S,9S; 7R,9R)]. After the reaction, acetone was distilled off from the reaction mixture, and the residue was extracted with 25 ml of chloroform twice. The extracts were washed with water, dried over sodium sulfate, and concentrated to dryness.

The product was treated with a crosslinked dextran gel (for example, Sephadex LH-20, a tradename for a product of Pharmacia Fire Chemicals) using acetone, and then the acetone was distilled off to give the desired product [a mixture of a racemic mixture (7S,9R; 7R,9S) and a racemic mixture (7S,9S; 7R,9R)]. The above stereoisomeric mixture was chromatographed on a column of silica gel using benzene/ethyl acetate (16/1), benzene/ethyl acetate (12/1), benzene/ethyl acetate (8/1) and then benzene/ethyl acetate (4/1) to give 41 mg of a stereoisomer (7S,9S; 7R,9R) of the above compound as a yellow solid and 21 mg of a stereoisomer (7S,9R; 7R,9S) of the above compound as a yellow solid.

Step E'

Epimerization of 4-demethoxy-11-deoxydaunomycinone (7S,9R; 7R,9S) to its isomer (7S,9S; 7R,9R)

24 mg of the above (7S,9R; 7R,9S) isomer was dissolved in 15 ml of acetone, and 1.5 ml of 60% perchloric acid was added. The reaction was carried out at room temperature for 3 hours. The reaction mixture was worked up and purified in the same way as in step E to give 12 mg of 4-demethoxy-11-deoxydaunomycinone (7S,9S; 7R,9R).

Melting point: 199°-207° C. (decomp.)

| NMRδ: 100 MHz CDCl₃ | | |
|---|---|---|
| 2.0–2.5 | (m) | —CH₂—at 8-position |
| 2.44 | (s) | —C(=O)—CH₃ at 9-position |
| 3.14 | (AB) | —CH₂—at 10-position |
| 3.65 | | —OH at 7-position |
| 4.60 | (s) | —OH at 9-position |
| 5.36 | (m) | —H at 7-position |
| 7.60 | (s) | —H at 11-position |
| 7.7 ~ 7.9 | (m) | —H at 2- and 3-positions |
| 8.2 ~ 8.4 | (m) | —H at 1- and 4-positions |
| 13.23 | (s) | —OH at 6-position |

EXAMPLE 2

Production of 14-O-acetyl-4-demethoxy-11-deoxyadriamycinone

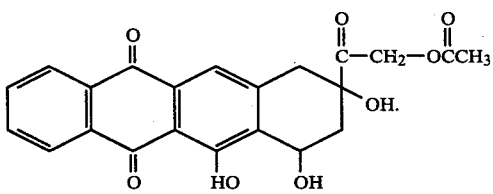

Step A

14-O-Acetyl-4-demethoxy-7,11-dideoxyadriamycinone

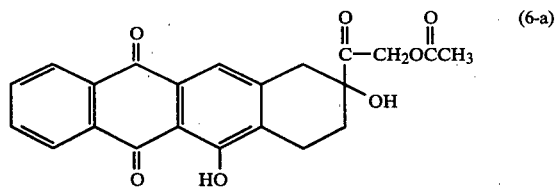

(6-a)

110 mg of the compound (4) obtained in step C of Example 1 was dissolved in 12 ml of tetrahydrofuran, and 200 mg of N-bromosuccinimide (NBS) was added four times at 1-hour intervals. The reaction was carried out at room temperature for a total period of 6 hours. The reaction mixture was poured into 200 ml of water, and extracted with 100 ml of carbon tetrachloride two times. The extracts were dried over sodium sulfate, and concentrated to dryness under reduced pressure. The product, without isolation and purification, was dissolved in 40 ml of acetone, and 200 mg of potassium acetate was added. The reaction was carried out at room temperature for 8 hours. After the reaction, the reaction mixture was poured into 50 ml of water, extracted with 25 ml of chloroform four times, dried over sodium sulfate, and then concentrated to dryness.

The product was chromatographed on a column of silica gel using benzene/ethyl acetate (40/1), benzene/ethyl acetate (30/1), benzene/ethyl acetate (20/1), and then benzene/ethyl acetate (15/1) as an eluant to give 83 mg of the title compound.

Melting point: 206°–209° C. (Decomp.)

| NMRδ: 100 MHz CDCl₃ | | |
|---|---|---|
| 2.0 ~ 2.3 | (m) | —CH₂— at 8-position |
| 2.20 | (s) | —OC(=O)—CH₃ |
| 2.79 | (s) | —OH at 9-position |
| 2.8 ~ 3.5 | (m) | —CH₂ at 7-and 10-positions |
| 5.11 | (s) | —CCH₂—OCCH₃ (with two C=O) |
| 7.60 | (s) | —H at 11-position |
| 7.75 ~ 7.9 | (m) | —H at 2-and 3-positions |
| 8.2 ~ 8.4 | (m) | —H at 1-and 4-positions |
| 13.03 | (s) | —OH at 6-position |

Step B

14-O-Acetyl-4-demethoxy-11-deoxyadriamycinone 51 mg of the compound (6-a) was dissolved in 14 ml of chloroform, and 12 ml of water and 16 mg of azobis-isobutyronitrile were added. To the solution was added 0.5 ml of a 0.8% (W/V) bromine in carbon tetrachloride solution in seven portions at 1-hour intervals at room temperature, and the reaction was carried out for 9 hours. After the reaction, the unreacted bromine, carbon tetrachloride and chloroform were distilled off. The residue was dissolved in 40 ml of ethyl acetate, and 10 ml of a 0.1 N aqueous solution of sodium hydrogen carbonate was added. The mixture was stirred at room temperature for a day and night. After the reaction, the reaction mixture was subjected to a separating procedure. The ethyl acetate layer was washed with water, dried over sodium sulfate, and concentrated to dryness. The dried product was chromatographed in the same way as in step A to give 34 mg of a racemic mixture (7S,9S; 7R,9R) of the title compound.

Melting point: 198°–205° C. (decomp.)

| NMRδ: 100 MHz CDCl₃ | | |
|---|---|---|
| 2.0 ~ 2.6 | (m) | —CH₂— at 8-position |
| 2.19 | (s) | OC(=O)—CH₃ |
| 3.28 | | —OH at 7-position |
| 3.22 | (AB) | —CH₂— at 10-position |
| 4.69 | (s) | —OH at 9-position |
| 5.25 | (AB) | —C(=O)—CH₂—OC(=O)CH₃ |
| 5.42 | (m) | —H at 7-position |
| 7.68 | (s) | —H at 11-position |
| 7.75 ~ 7.9 | (m) | —H at 2-and 3-positions |
| 8.25 ~ 8.4 | (m) | —H at 1-and 4-positions |
| 13.40 | (s) | —OH at 6-position |

IR (cm⁻¹) 3450, 2950, 1750, 1730, 1670, 1630, 1590, 1480, 1420, 1385, 1360, 1330, 1285, 1270, 1245, 1215, 1160, 1110, 1100, 1065, 1060, 1040, 1030, 1010, 980, 960, 930, 910, 870, 840, 830, 820, 795, 770, 745, 715.

EXAMPLE 3

Production of 4-demethoxy-11-deoxydaunomycin

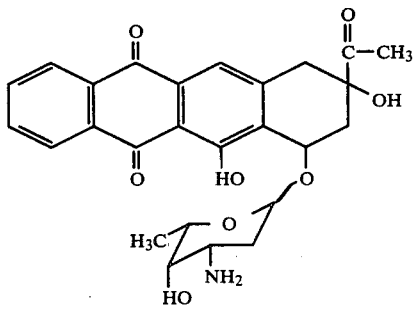

| NMRδ: 100 MHz CDCl₃ | | |
|---|---|---|
| 1.32 | (d) | —CH₃ at 6-position |
| 4.36 | (broad q) | H at 5-position |
| 4.62 | (td) | H at 2-position |
| 5.05 | (m) | H at 3-position |
| 5.66 | (broad d) | H at 4-position |
| 6.15 | (broad d) | —NHCOCF₃ |
| 6.65 | (dd) | H at 1-position |
| 8.15 ~ 8.4 | (m) | —CO—⌬—NO₂ |

Step A

4-O-p-nitrobenzoyl-1,2,3,6-tetradeoxy-3-trifluoroacetamide-L-lyxo-hex-1-enopyranose

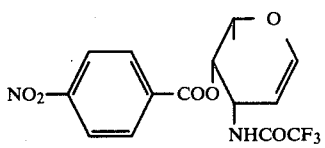

(1) 104 mg of N-trifluoroacetyldaunosamine was dissolved in anhydrous pyridine, and 300 mg of p-nitrobenzoyl chloride was added. With ice cooling (about 8° C.), the reaction was carried out for 22 hours. After the reaction, the reaction mixture was poured into 100 ml of ice water to destroy the excess reagent. The reaction mixture was then extracted with 30 ml of chloroform three times. In order to remove pyridine from the extracts, the extracts were subjected to a separating procedure using 50 ml of 1 N hydrochloric acid. The chloroform layer was washed with water, dried over sodium sulfate, and concentrated.

(2) The concentrate (crude 1,4-bis-O-p-nitrobenzoyl-N-trifluoroacetyldaunosamine) was dissolved in 10 ml of acetone, and 5 ml of 4 N hydrochloric acid was added. The reaction was carried out at room temperature for 10 hours to partially hydrolyze the p-nitrobenzoyl group. After the reaction, the acetone was removed by concentration, and 15 ml of water was added. The mixture was extracted with 10 ml of chloroform three times. The extracts were subjected to a separating procedure using 10 ml of a 0.1 N aqueous solution of sodium hydrogen carbonate. The chloroform layer was washed with water, dried over sodium sulfate, and concentrated.

(3) The concentrate (crude 4-O-p-nitrobenzoyl-N-trifluoroacetyldaunosamine) was dissolved in 15 ml of anhydrous pyridine, and 600 mg of p-toluenesulfonyl chloride was added. The reaction was carried out at 80° C. for 18 hours. The light brown reaction mixture was poured into 100 ml of ice water to destroy the excess reagent. The reaction mixture was then extracted with 30 ml of benzene four times. The extracts were washed with water, dried over sodium sulfate, and concentrated. The oily product was chromatographed on a column of silica gel using benzene/ethyl acetate (25/1) as an eluant to give 118 mg of the title compound.

Melting point: 144°–148° C.

[α]$_D^{26}$: −100° C. (c: 0.5, acetone)

Step B

4-Demethoxy-4′-O-p-nitrobenzoyl-11-deoxy-3′-N-trifluoroacetyldaunomycin

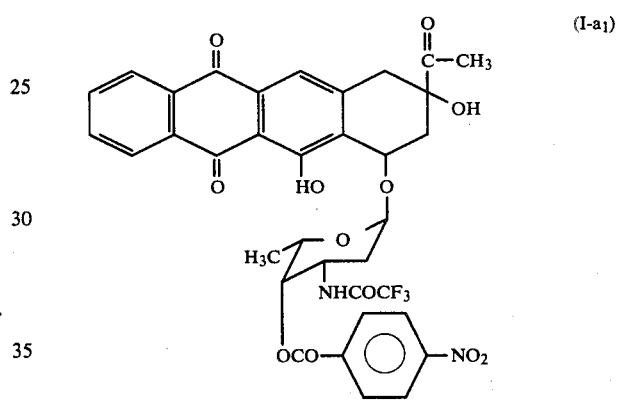

(I-a₁)

20 mg of the 4-demethoxy-11-deoxydaunomycinone 7S,9S; 7R,9R) obtained by the method of Example 1 and 80 mg of glycal obtained in step A above were dissolved in 2 ml of benzene. A catalytic amount of p-toluenesulfonic acid was added, and the reaction carried out at room temperature for 93 hours. After the reaction, the reaction mixture was poured into 30 ml of a 0.01 N aqueous solution of sodium hydrogen carbonate, and extracted with 15 ml of benzene three times. The extracts were washed with water, dried over sodium sulfate, and concentrated to dryness. The product was chromatographed on a silica gel column using benzene/ethyl acetate (4/1) as an eluent, further chromatographed on a column of a crosslinked dextran gel (e.g. Sephadex LH-20) using chloroform/acetone (1/2) as an eluent; and further chromatographed on a column of silica gel using benzene/ethyl acetate (4/1) as an eluent to isolate the individual stereoisomers of the title compound. The isolated crude products were again treated individually with Sephadex LH-20 to give 7 mg of a (7S,9S,1′α) isomer (I-a₁-1) of the title compound, 3 mg of a (7S,9S,1′β) isomer (I-a₁-2) of the title compound, 10 mg of a (7R,9R,1′α) isomer (I-a₁-3) of the title compound, and 3 mg of a (7R,9R,1′β) isomer (I-a₁-4) of the title compound.

(I-a₁-1)

Melting point: 153°–156° C.

[α]$_D^{24}$: −125° C. (c: 0.2, acetone)

| NMRδ: 100 MHz CDCl₃ | | |
|---|---|---|
| 1.27 | (s) | —CH₃ at 6'-position |
| 2.0 ~ 2.5 | (m) | —CH₂ at 8-and 2'-positions |
| 2.43 | (s) | —COCH₃ at 9-position |
| 3.21 | (AB) | —CH₂ at 10-position |
| 4.25 | (s) | —OH at 9-position |
| 4.3 ~ 4.7 | (m) | —H at 3'-position |
| 4.48 | (broad q) | —H at 5'-position |
| 5.34 | (m) | —H at 7-position |
| 5.51 | (m) | —H at 4'-position |
| 5.69 | (m) | —H at 1'-position |
| 6.40 | (broad d) | NHCOCF₃ |
| 7.64 | (s) | —H at 11-position |
| 7.7 ~ 7.9 | (m) | —H at 2-and 3-positions |
| 8.2 ~ 8.45 | (m) | —H at 1-and 4-positions (—CO—C₆H₄—NO₂) |
| 13.33 | (s) | —OH at 6-position |

(I-a₁-2)

Melting point: 142°–145° C.
$[\alpha]_D^{24}$: +87.5° (c: 0.2, acetone)

| NMRδ: 100 MHz CDCl₃ | | |
|---|---|---|
| 1.07 | (d) | —CH₃ at 6'-position |
| 1.7 ~ 2.6 | (m) | —CH₂ at 8-and 2'-positions |
| 2.39 | (s) | —COCH₃ at 9-positions |
| 3.27 | (broad s) | —CH₂ at 10-position |
| 3.84 | (broad q) | —H at 5'-position |
| 4.2 ~ 4.6 | (m) | —H at 3'-position |
| 4.74 | (broad s) | —OH at 9-position |
| 5.15 | (dd) | —H at 1'-position |
| 5.32 | (m) | —H at 4'-position |
| 5.66 | (m) | —H at 7-position |
| 6.54 | (broad d) | NHCOCF₃ |
| 7.61 | (s) | —H at 11-position |
| 7.75 ~ 7.9 | (m) | —H at 2-and 3-positions |
| 8.1 ~ 8.4 | (m) | —H at 1-and 4-positions (—CO—C₆H₄—NO₂) |
| 13.36 | (s) | OH at 6-position |

(I-a₁-3)

Melting point: 148°–152° C.
$[\alpha]_D^{25}$: −225° C. (c: 0.2, acetone)

| NMRδ: 100 MHz CDCl₃ | | |
|---|---|---|
| 1.26 | (d) | —CH₃ at 6'-position |
| 1.6 ~ 2.7 | (m) | —CH₂ at 8-and 2'-positions |
| 2.39 | (s) | —COCH₃ at 9-position |
| 3.24 | (broad s) | —CH₂ at 10-position |
| 4.52 | (s) | —OH at 9-position |
| 4.45 ~ 4.8 | (m) | —H at 3'-position |
| 4.73 | (broad q) | —H at 5'-position |
| 5.44 | (m) | —H at 4'-position |
| 5.5 ~ 5.57 | (m) | —H at 7-and 1'-positions |
| 6.62 | (broad d) | —NHCOCF₃ |
| 7.61 | (s) | —H at 11-position |

| NMRδ: 100 MHz CDCl₃ | | |
|---|---|---|
| 7.75 ~ 7.95 | (m) | —H at 2-and 3-positions |
| 8.2 ~ 8.4 | (m) | —H at 1-and 4-positions (—CO—C₆H₄—NO₂) |
| 13.43 | (2) | —OH at 6-position |

(I-a₁-4)

Melting point: 190°–195° C.
$[\alpha]_D^{25}$: −137.5° (c: 0.2, acetone)

| NMRδ: 100 MHz CDCl₃ | | |
|---|---|---|
| 1.32 | (d) | —CH₃ at 6'-position |
| 1.6 ~ 2.85 | (m) | —CH₂ at 8-and 2'-positions |
| 3.17 | (AB) | —CH₂ at 10-position |
| 4.01 | (broad q) | —H at 5'-position |
| 4.25 ~ 4.6 | (m) | —H at 3'-position |
| 4.55 | (s) | —OH at 9-position |
| 5.20 | (dd) | —H at 1'-position |
| 5.3 ~ 5.45 | (m) | —H at 7-and 4-position |
| 6.59 | (broad d) | —NHCOCF₃ |
| 7.57 | (s) | —H at 11-position |
| 7.7 ~ 7.9 | (m) | —H at 2-and 3-positions |
| 8.15 ~ 8.4 | (m) | —H at 1-and 4-positions (—CO—C₆H₄—NO₂) |
| 13.25 | (m) | —OH at 6-position |

Step C

4-Demethoxy-11-deoxydaunomycin (I-1)

12 mg of N-trifluoroacetyl-4'-O-p-nitrobenzoyl-daunomycin (7S,9S,1'α) (I-a₁-1) was dissolved in methanol, and 1 ml of a 10% aqueous solution of potassium carbonate was added. Under ice cooling (about 8° C.), the reaction was carried out for 12 hours. After the reaction, 15 ml of water was added, and the reaction mixture was extracted with 10 ml of chloroform four times. The chloroform layer was treated with 5 ml of 0.5% aqueous acetic acid four times. The acetic acid layer was neutralized with a 1 N aqueous solution of sodium hydrogen carbonate, and again extracted with chloroform. The extract was dried over sodium sulfate, and concentrated to dryness. The dried solid was dissolved in dichloromethane/t-butanol (1/20) and lyophilized to give 7.5 mg of a (7S,9S,1'α) isomer (I-1a) of the title compound as a yellow powder.

In the same way as above, 4.2 mg of a (7S,9S,1'β) isomer (I-1b) of the title compound was prepared from 7.9 mg of (I-a₁-2); 6.5 mg of a (7R,9R,1'α) isomer (I-1c) of the title compound, from 11 mg of (I-a₁-3); and 3.6 mg of a (7R,9R,1'β) isomer (I-1d) of the title compound, from 6.3 mg of (I-a₁-4).

(I-1a)

Melting point: 202°–212° C. (Decomp.)
$[\alpha]_D^{24}$: +50° (c: 0.1, methanol)

| FDMS: MH⁺ 482 NMRδ: 100 MHz CDCl₃ | | |
|---|---|---|
| 1.28 | (d) | CH₃ at 6'-position |
| 1.6 ~ 2.6 | (m) | —CH₂ at 8- and 2'-positions |
| 2.39 | (s) | —COCH₃ at 9-position |
| 3.0 ~ 3.2 | (m) | —H at 3'-position |
| 3.24 | (AB) | —CH₂ at 10-position |
| 3.44 | (m) | —H at 4'-position |
| 4.28 | (broad q) | —H at 5'-position |
| 5.36 | (m) | —H at 7-position |
| 5.55 | (m) | —H at 1'-position |
| 7.64 | (s) | —H at 11-position |
| 7.75 ~ 7.95 | (m) | —H at 2- and 3-positions |
| 8.25 ~ 8.45 | (m) | —H at 1- and 4-positions |

IR (cm⁻¹) 3450, 2910, 1705, 1665, 1630, 1590, 1515, 1480, 1455, 1420, 1385, 1355, 1325, 1300, 1275, 1250, 1200, 1115, 1005, 980, 940, 875, 825, 795, 770, 715.

(I-1b)

Melting point: 160°–172° C. (decomp.)
$[\alpha]_D^{22}$: +500° (c: 0.1, methanol)

| FDMS: MH⁺ 482 NMRδ: 100 MHz CDCl₃ | | |
|---|---|---|
| 1.25 | (d) | —CH₃ at 6'-position |
| 1.55 ~ 2.7 | (m) | —CH₂ at 8- and 2'-positions |
| 2.49 | (s) | —COCH₃ at 9-position |
| 2.95 ~ 3.2 | (m) | —H at 3'-position |
| 3.3 ~ 3.45 | | —CH— at 10-position —H at 4'-position |
| 3.60 | (broad q) | —H at 5'-position |
| 5.00 | (dd) | —H at 1'-position |
| 5.68 | (m) | —H at 7-position |
| 7.61 | (s) | —H at 11-position |
| 7.75 ~ 7.95 | (m) | —H at 2- and 3-positions |
| 8.2 ~ 8.4 | (m) | —H at 1- and 4-positions |

IR (cm⁻¹) 3400, 2900, 1705, 1670, 1630, 1590, 1480, 1420, 1385, 1360, 1330, 1300, 1275, 1255, 1205, 1165, 1115, 1060, 980, 920, 870, 830, 775, 720.

(I-1c)

Melting point: 180° ~ 195° C. (decomp.)
$[\alpha]_D^{26}$: −150° (c: 0.1, methanol)

| FDMS: MH⁺ 482 NMRδ: 100 MHz CDCl₃ | | |
|---|---|---|
| 1.36 | (d) | —CH₃ at 6'-position |
| 1.6 ~ 2.5 | (m) | —CH₂ at 8- and 2'-positions |
| 2.40 | (s) | —COCH₃ at 9-position |
| 2.9 ~ 3.2 | (m) | —H at 3'-position |
| 3.21 | (AB) | —CH₂ at 10-position |
| 3.48 | (m) | —H at 4'-position |
| 4.11 | (broad q) | —H at 5'-position |
| 5.32 | (m) | —H at 7-position |
| 5.50 | (m) | —H at 1'-position |
| 7.65 | (s) | —H at 11-position |
| 7.75 ~ 7.9 | (m) | —H at 2- and 3-positions |
| 8.25 ~ 8.45 | (m) | —H at 1- and 4-positions |

IR (cm⁻¹) 3450, 2900, 1710, 1670, 1630, 1590, 1480, 1420, 1385, 1360, 1330, 1300, 1270, 1250, 1200, 1160, 1120, 1080, 1010, 980, 930, 875, 825, 790, 770, 715.

(I-1d)

Melting point: 185° ~ 195° C. (decomp.)
$[\alpha]_D^{22}$: −400° (c: 0.1, methanol
FDMS: MH⁺482

| NMRδ: 100 MHz CDCl₃ | | |
|---|---|---|
| 1.39 | (d) | —CH₃ at 6'-position |
| 1.35 ~ 2.85 | (m) | —CH₂ at 8- and 2'-positions |
| 2.42 | (s) | —COCH₃ at 9-position |
| 2.9 ~ 3.2 | (m) | —H at 3'-position |
| 3.15 | (AB) | —CH₂ at 10-position |
| 3.38 | (m) | —H at 4'-position |
| 3.66 | (broad q) | —H at 5'-position |
| 5.00 | (dd) | —H at 1'-position |
| 5.33 | (m) | —H at 7-position |
| 7.64 | (s) | —H at 11-position |
| 7.7 ~ 7.9 | (m) | —H at 2- and 3-positions |
| 8.2 ~ 8.4 | (m) | —H at 1- and 4-positions |

IR (cm⁻¹) 3450, 2900, 1710, 1670, 1630, 1590, 1480, 1420, 1390, 1360, 1330, 1300, 1280, 1255, 1210, 1170, 1130, 1110, 1065, 1025, 985, 920, 870, 830, 790, 780, 720.

EXAMPLE 4

Production of 4-demethoxy-11-deoxyadriamycin

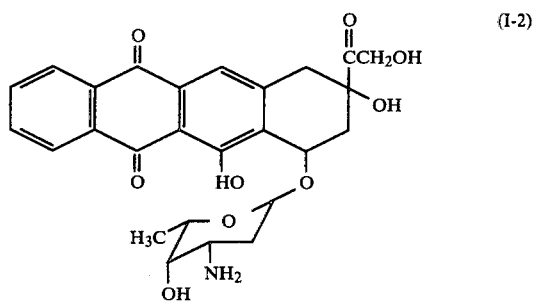

(I-2)

Step A

14-O-acetyl-4-demethoxy-4'-O-p-nitrobenzoyl-11-deoxy-3'-N-trifluoroacetyladriamycin:

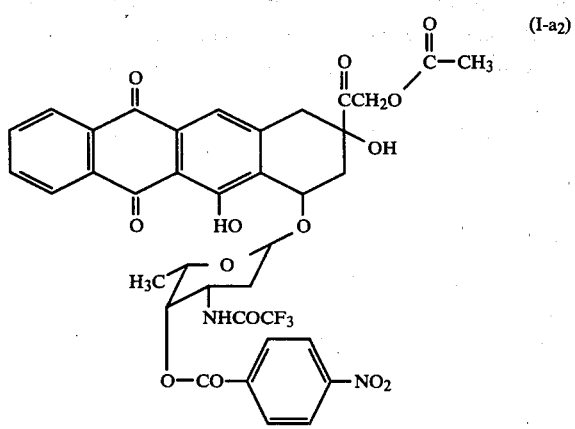
(I-a₂)

32 mg of the 14-O-acetyl-4-demethoxy-11-deoxyadriamycinone (7S,9S; 7R,9R) obtained by the method of Example 2 and 120 mg of the glycal obtained in step A of Example 3 were dissolved in 12 ml of dichloromethane. A catalytic amount of p-toluenesulfonic acid was added, and the reaction was carried out at room temperature for 75 hours. After the reaction, the reaction mixture was poured into 10 ml of a 0.01 N aqueous solution of sodium hydrogen carbonate, and was extracted with 10 ml of dichloromethane two times. The extracts were washed with water, dried over sodium sulfate, and concentrated to dryness.

The product was worked up in the same way as in the purifying procedure in step B of Example 3 to give 10 mg of a (7S,9S, 1'α) isomer (I-a₂-1) of the title compound and 10.7 mg of a (7R,9R, 1'α) isomer (I-a₂-2) of the title compound.

(I-a₂-1)

Melting point: 154°–157° C.
$[α]_D^{25}$: −125° (c: 0.2, acetone)

| NMRδ: 100 MHz CDCl₃ | | |
|---|---|---|
| 1.31 | (d) | —CH₃ at 6'-position |
| 1.9 ~ 2.7 | (m) | —CH₂ at 8-and 2'-positions |
| 2.22 | (s) | OCOCH₃ |
| 3.31 | (AB) | —CH₂ at 10-position |
| 4.41 | (s) | —OH at 9-position |
| 4.3 ~ 4.7 | (m) | —H at 3'-position |
| 4.45 | (broad q) | —H at 5'-position |
| 5.24 | (AB) | —CCH₂—OCOCH₃ (C=O) |
| 5.40 | (m) | —H at 7-position |
| 5.50 | (m) | —H at 4'-position |
| 5.70 | (m) | —H at 1'-position |
| 6.30 | (broad d) | —NH—COCF₃ |
| 7.69 | (s) | —H at 11-position |
| 7.75 ~ 7.95 | (m) | —H at 2-and 3-positions |
| 8.2 ~ 8.45 | (m) | —H at 1-and 4-positions (—CO—C₆H₄—NO₂) |
| 13.38 | (s) | —OH at 6-position |

(I-a₂-2)

Melting point: 155°–160° C.
$[α]_D^{25}$: −225° (c: 0.2, acetone)

| NMRδ: 100 MHz CDCl₃ | | |
|---|---|---|
| 1.26 | (d) | —CH₃ at 6'-position |
| 1.8 ~ 2.8 | (m) | —CH₂ at 8-and 2'-positions |
| 2.20 | (s) | OCOCH₃ |
| 3.31 | (broad s) | —CH₂ at 10-position |
| 4.4 ~ 4.85 | (m) | —H at 3'-position |
| 4.72 | (broad q) | —H at 5'-position |
| 4.62 | (s) | —OH at 9-position |
| 5.21 | (AB) | —CO—CH₂—OCOCH₃ |
| 5.41 | (m) | —H at 4'-position |
| 5.5 ~ 5.65 | (m) | —H at 7-and 1'-positions |
| 6.52 | (broad d) | NH—COCF₃ |
| 7.63 | (s) | —H at 11-position |
| 7.75 ~ 7.95 | (m) | —H at 2-and 3-positions |
| 8.2 ~ 8.4 | (m) | —H at 1-and 4-positions (—CO—C₆H₄—NO₂) |
| 13.46 | (s) | —OH at 6-position |

Step B

4-Demethoxy-11-deoxyadriamycin (1) 12.3 mg of the compound (I-a₂-1) obtained in step A was dissolved in 6 ml of methanol, and 0.06 ml of a 10% aqueous solution of potassium carbonate was added. The reaction was carried out at 0° C. for 3 hours. After the reaction, 30 ml of water was added, and extracted with 10 ml of chloroform three times. The extracts were washed with water, dried with sodium sulfate, and concentrated to dryness. The dried product was crude N-trifluoroacetyl-4-demethoxy-11-deoxyadriamycin (7S,9S, 1'-α).

(2) The dried crude product was dissolved in 3 ml of dichloromethane, and 1.2 ml of triethoxymethane and a catalytic amount of p-toluenesulfonic acid were added. The reaction was carried out at room temperature for 2.5 hours. After the reaction, 15 ml of a 0.1 N aqueous solution of sodium hydrogen carbonate was added to neutralize the reaction mixture, followed by extraction with dichloromethane. The extract was dried over sodium sulfate, and concentrated to dryness.

(3) The resulting dried product was dissolved in 4 ml of methanol, and 1 ml of a 10% aqueous solution of potassium carbonate was added. With ice cooling (about 8° C.), the reaction was carried out for 16 hours. After the reaction, 15 ml of water was added, and the reaction mixture was extracted with chloroform. The extract was treated with a 1% aqueous solution of acetic acid (when the orthoformate was eliminated). The acetic acid layer was adsorbed onto an adsorbent resin (e.g. Amberlite XAD-2, a tradename for a product of Rohm & Haas Co.), and eluted stepwise with acetone/0.0001 N hydrochloric acid (20/80, acetone/0.0001 N hydrochloric acid (30/70), and then acetone/0.0001 N hydrochloric acid (40/60). After distilling off the acetone, the eluates were lyophilized to give 3.0 mg of the hydrochloride of a (7S,9S,1'α) isomer (I-2-1) of 4-demethoxy-11-deoxyadriamycin as a yellow powder.

9.8 mg of the compound (I-a₂-2) obtained in step A was similarly treated to give 2.5 mg of the hydrochloride of a (7R,9R,1'α) isomer (I-2-2) of 4-demethoxy-11-deoxyadriamycin.

Hydrochloride of (I-2-1)

Melting point: 158°-170° C. (decomp.)
[α]$_D^{24}$: +75° (c: 0.1, water)
FDMS MH+ 498

| NMRδ: 100 MHz D₂O | | |
|---|---|---|
| 1.80 | (d) | —CH₃ at 6'-position |
| 2.4 ~ 2.9 | (m) | —CH₂ at 8-and 2'-positions |
| 3.45 | (broad s) | —CH₂ at 10-position |
| 4.1 ~ 4.4 | (m) | —H at 3'-position |
| 4.33 | (m) | —H at 4'-position |
| 4.66 | (broad q) | —H at 5'-position |
| 5.30 | (s) | —C(O)—CH₂—OH |
| 5.94 | (m) | —H at 1'-position |
| 7.53 | (s) | —H at 11-position |
| 8.2 ~ 8.5 | (m) | —H at 1-, 2-, 3-and 4-positions |

IR (cm⁻¹) 3400, 2900, 1720, 1670, 1630, 1590, 1510, 1480, 1420, 1385, 1360, 1330, 1300, 1275, 1250, 1200, 1115, 1080, 1060, 1010, 980, 940, 910, 875, 825, 770, 715.

Hydrochloride of (I-2-2)

Melting point: 145°-155° C. (decomp.)
[α]$_D^{25}$: −125° (c: 0.1, water)
FDMS MH+ 498

| NMRδ: 100 MHz D₂O | | |
|---|---|---|
| 1.73 | (d) | —CH₃ at 6'-position |
| 2.3 ~ 3.2 | (m) | —CH₂ at 8- and 2'-positions |
| 3.50 | (broad s) | —CH₂ at 10-position |
| 4.1 ~ 4.3 | (m) | —H at 3'-position |
| 4.32 | (m) | —H at 4'-position |
| 4.84 | (broad q) | —H at 5'-position |
| 5.33 | (s) | —C(O)—CH₂—OH |
| 5.47 | (m) | —H at 7-position |
| 5.91 | (m) | —H at 1'-position |
| 7.48 | (s) | —H at 11-position |
| 8.2 ~ 8.5 | (m) | —H at 1-, 2-, 3- and 4-positions |

IR (cm⁻¹) 3450, 2900, 1720, 1670, 1630, 1590, 1480, 1425, 1390, 1365, 1330, 1300, 1280, 1255, 1195, 1110, 1075, 1010, 985, 935, 910, 830, 790, 770, 715.

EXAMPLE 5

Salt Formation

Illustrative of the procedures which may be used to prepare acid addition salts, the free base of 4-demethoxy-11-deoxyadriamycin (7S,9S,1'α) and 4-demethoxy-11-deoxydaunomycin (7S,9S,1'α) may be dissolved in ethyl acetate and about one equivalent of HCl added. On lyophilization, the appropriate hydrochloride salt is obtained.

Acid addition salts of the other anthracycline glycoside compounds of formula I may be prepared in a similar manner by using the appropriate organic or inorganic acid and appropriate free base starting material.

We claim:

1. An anthracycline glycoside of the general formula

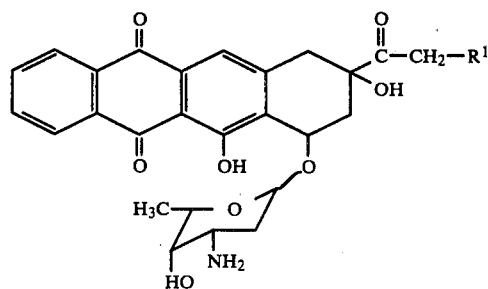

wherein R¹ represents hydrogen, hydroxyl or (lower)alkanoyloxy, or a nontoxic acid addition salt thereof.

2. A compound according to claim 1 wherein R¹ is hydrogen or hydroxyl, or a nontoxic acid addition salt thereof.

3. A compound according to claim 1 or claim 2 having a (7S,9S) configuration.

4. A compound according to claim 1 or claim 2 wherein the amino sugar residue has a 1'α linkage.

5. The anthracycline glycoside of the formula

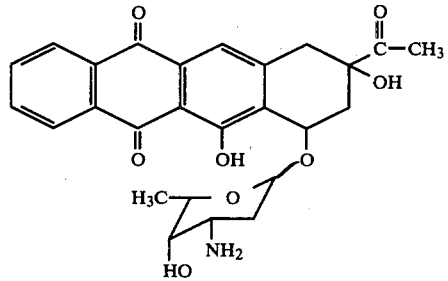

or a nontoxic acid addition salt thereof.

6. The isomer of the compound according to claim 5 which has the configuration (7S,9S,1'α), or a nontoxic acid addition salt thereof.

7. The isomer of the compound according to claim 5 which has the configuration (7S,9S,1'β), or a nontoxic acid addition salt thereof.

8. The isomer of the compound according to claim 5 which has the configuration (7R,9R,1'α), or a nontoxic acid addition salt thereof.

9. The isomer of the compound according to claim 5 which has the configuration (7R,9R,1'β), or a nontoxic acid addition salt thereof.

10. The anthracycline glycoside of the formula

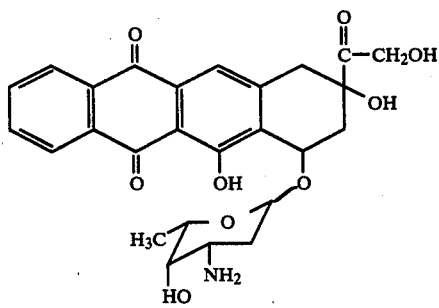

or a nontoxic acid addition salt thereof.

11. The isomer of the compound according to claim 10 which has the configuration (7S,9S,1'α), or a nontoxic acid addition salt thereof.

12. The isomer of the compound according to claim 10 which has the configuration (7R,9R,1'α), or a nontoxic acid addition salt thereof.

13. An aglycone intermediate of the formula

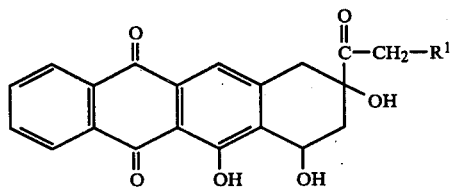

wherein $R^1$ represents hydrogen, hydroxyl or (lower)alkanoyloxy.

14. The compound according to claim 13 wherein $R^1$ is hydrogen.

15. The compound according to claim 13 wherein $R^1$ is hydroxyl.

16. The compound according to claim 13 wherein $R^1$ is (lower)alkanoyloxy.

17. The compound according to claim 16 wherein $R^1$ is acetoxy.

18. A compound according to claim 13, 14, 15, 16 or 17 in the form of the racemic mixture (7S,9S; 7R,9R).

19. An intermediate of the formula

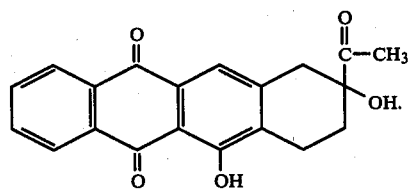

20. A pharmaceutical composition for use in therapeutically treating a mammalian host affected by a microbial infection comprising a therapeutically effective amount of a compound as claimed in claim 1 and a pharmaceutical carrier or diluent.

21. A pharmaceutical composition for use in therapeutically treating a mammalian host affected by L 1210 leukemia comprising a tumor-inhibiting amount of a compound as claimed in claim 1 and a pharmaceutical carrier or diluent.

* * * * *